(12) United States Patent
Danley

(10) Patent No.: US 6,843,595 B2
(45) Date of Patent: Jan. 18, 2005

(54) DIFFERENTIAL SCANNING CALORIMETER ACCOUNTING FOR HEAT LEAKAGE

(75) Inventor: Robert L. Danley, Collingswood, NJ (US)

(73) Assignee: Waters Investment Limited, New Castle, DE (US)

(*) Notice: Subject to any disclaimer, the term of this patent is extended or adjusted under 35 U.S.C. 154(b) by 0 days.

(21) Appl. No.: 10/382,580

(22) Filed: Mar. 7, 2003

(65) Prior Publication Data

US 2003/0179806 A1 Sep. 25, 2003

Related U.S. Application Data

(63) Continuation-in-part of application No. 09/769,313, filed on Jan. 26, 2001, now Pat. No. 6,561,692.
(60) Provisional application No. 60/362,546, filed on Mar. 8, 2002.

(51) Int. Cl.[7] ..................... G01K 25/00; G01K 17/004; G01K 17/06
(52) U.S. Cl. ..................... 374/10; 374/29; 374/31; 374/39
(58) Field of Search ..................... 374/10–12, 29, 374/31, 39, 13, 43, 1, 32

(56) References Cited

U.S. PATENT DOCUMENTS

| | | | | |
|---|---|---|---|---|
| 4,255,961 A | * | 3/1981 | Biltonen et al. | 374/11 |
| 4,530,608 A | | 7/1985 | O'Neill | |
| 4,783,174 A | * | 11/1988 | Gmelin et al. | 374/33 |
| 5,098,196 A | * | 3/1992 | O'Neill | 374/11 |
| 5,224,775 A | | 7/1993 | Reading et al. | |
| 5,711,604 A | * | 1/1998 | Nakamura | 374/44 |
| 5,806,979 A | * | 9/1998 | Gschneidner et al. | 374/34 |
| 5,842,788 A | * | 12/1998 | Danley et al. | 374/12 |
| 5,967,659 A | * | 10/1999 | Plotnikov et al. | 374/11 |
| 5,988,875 A | * | 11/1999 | Gershfeld et al. | 374/10 |
| 6,079,873 A | * | 6/2000 | Cavicchi et al. | 374/10 |
| 6,170,984 B1 | * | 1/2001 | Schawe et al. | 374/10 |
| 6,239,415 B1 | * | 5/2001 | Paulik et al. | 219/497 |
| 6,431,747 B1 | | 8/2002 | Danley | |
| 6,488,406 B2 | | 12/2002 | Danley | |
| 6,508,585 B2 | * | 1/2003 | Nakamura et al. | 374/12 |
| 6,648,504 B2 | * | 11/2003 | Danley | 374/43 |

FOREIGN PATENT DOCUMENTS

| | | | |
|---|---|---|---|
| EP | 1 136 802 | 9/2001 | |
| EP | 1 139 083 | 10/2001 | |
| EP | 03 00 5237 | 6/2003 | |
| JP | 60080748 A | * 5/1985 | G01N/25/20 |

OTHER PUBLICATIONS

W. Hemminger and G. Hohne, Calorimetry Fundamentals and Practice, (4.6 Inferences Concerning Calorimetry), Verlag Chemie, Weinheim, 1984, 76–79.

(List continued on next page.)

Primary Examiner—Gail Verbitsky
(74) Attorney, Agent, or Firm—Shaw Pittman LLP

(57) ABSTRACT

A method and system for calculating a heat flow to a sample in a differential scanning calorimeter (DSC). The DSC has a sensor within an enclosure comprising an absolute temperature measurement detector for measuring the temperature of a base position on the sensor, a first differential temperature detector for measuring the temperature difference between a sample position and the base position, and a second differential temperature detector for measuring the temperature difference between a reference position and a sample position. Thermal resistances and heat capacities of the DSC are calibrated. The DSC is operated, and the heat flow to the sample is calculated using a method that accounts for the leakage heat flows.

42 Claims, 7 Drawing Sheets

OTHER PUBLICATIONS

G. Hohne, "Problems with the Calibration of Differential–Temperature–Scanning–Calorimeters", Thermochimica Acta, 69, 1983, 175–197, (Elsevier Science Publishers, B.V.).

P. Claudy, J.C. Commercon, and J.M. Letoffe, "Heat Transfer in a Disc–Type DSC Apparatus", Thermochimica Acta, 65, 1983, 245–255 (Elsevier Science Publishers, B.V.).

W. Hemminger and G. Hohne, "Calorimetry Fundamentals and Practice", Verlag Chemie, Weinheim, 1994, 230–233.

P. Claudy, J.C. Commercon, and J.M. Letoffe, "Heat Transfer in a Disc–Type DSC Apparatus", Thermochimica Acta, 68, 1983, 305–316 (Elsevier Science Publishers, B.V.).

G. Jang and K. Rajeshwar, "Equivalent–Circuit Modeling of Heat–Flux Differential Scanning Calorimetry Cell. Analysis of Thermal Resistance Factors and Comparisio with Experimental Data", Anal. Chem., 581986, 416–421.

J.P. Holman, Heat Transfer (Lumped–Heat–Capacity System), McGraw–Hill, New York, $4^{th}$ Edition, 1976, 97–102.

R. Danley and P. Caulfield, "DSC Baseline Improvements Obtained by a New Heat Flow Measurement Technique", Proc. $29^{th}$ NATAS Conference, 2002, 667–672.

R. Danley and P. Caufield, "DSC Resolution and Dynamic Response Improvements Obtained by a New Heat Flow Measurement Technique", Proc. $29^{th}$ NATAS Conference, 2002, 673–678.

Communication from the European Patent Office dated Aug. 4,2004.

* cited by examiner

DIFFERENTIAL SCANNING CALORIMETER ACCOUNTING FOR HEAT LEAKAGE

The present application claims priority to U.S. Provisional Patent Application No. 60/362,546, filed Mar. 8, 2002, and is a continuation-in-part of 09/769,313, entitled "Heat Flux Differential Scanning Calorimeter Sensor," filed Jan. 26, 2001, now U.S. Pat. No. 6,561,692.

The present application incorporates by reference the following U.S. patents and patent applications: U.S. Pat. No. 6,431,747, entitled "Heat Flux Differential Scanning Calorimeter," issued Aug. 13, 2002; U.S. Pat. No. 6,488,406, entitled "Differential Scanning Calorimeter," issued Dec. 3, 2002; U.S. patent application Ser. No. 09/769,313, filed Jan. 26, 2001, entitled "Modulated Differential Scanning Calorimeter;" and U.S. patent application Ser. No. 10/085,054, filed Mar. 1, 2002, entitled "System and Method for Calibrating Contact Thermal Resistances in Differential Scanning Calorimeters."

BACKGROUND OF THE INVENTION

1. Field of the Invention

The present invention relates generally to differential scanning calorimeters (DSCs), and more specifically to methods of accounting for heat leakage in DSCs.

2. Background Information

A DSC is a symmetrical instrument, comprising a sample and reference calorimeter within a common thermal enclosure, where the two calorimeters are intended to be identical. DSCs have a sensor which measures the temperature difference between the sample and the reference position in the respective calorimeters. A sample to be analyzed is loaded into a pan and placed on the sample position of the sensor and an inert reference material is loaded into a pan and placed on the reference position of the sensor (alternatively, an empty pan is often used as the reference). The sensor is installed in an oven whose temperature is varied dynamically according to a desired temperature program. The temperature program for conventional DSCs typically includes combinations of linear temperature ramps and constant temperature segments. Modulated DSCs use a temperature program in which periodic temperature modulations are superimposed on linear ramps. Modulated DSCs are described in U.S. Pat. No. 5,224,775, which is incorporated by reference herein.

Conventional DSC Heat Flow Rate Measurement

In conventional DSCs, the measured quantities are the difference between the temperatures of the sample and reference sensors and the sample sensor temperature. During the dynamic portion of the DSC experiment, a differential temperature is created between the sample and reference positions on the sensor. The temperature difference is the result of the difference between the heat flow to the sample and the heat flow to the reference. The temperature difference is assumed to be proportional to the difference in heat flow to the sample as compared to the heat flow to the reference, thus the differential temperature may be used to measure the heat flow to the sample using the equation:

$$q = E(T)\Delta T$$

Where, $E(T)$ is a temperature dependent factor that reflects the proportionality of the measured differential temperature to the sample heat flow rate. A fundamental underlying assumption is that the sample and reference sides of the calorimeter are perfectly symmetrical. In reality the balance is less than perfect which is reflected in the observation that when the calorimeter is operated empty, the resulting heat flow rate signal is not zero as it should be if the DSC were symmetrical as assumed. Additionally, it is well known that the heat flow rate signal is smeared, as a result of the heat capacity of the sensor and pans and the differences in heating rate that exist between the sample and reference. The heating rate differences exist in conventional DSC during a transition or generally during a MDSC experiment. However, those shortcomings may be overcome by using the DSC apparatus and heat flow rate measurement methods disclosed below.

DSC Heat Flow Rate Measurement Including Sensor Asymmetry

FIG. 1 shows a thermal network model that may be used to represent heat flux in certain DSC sensors. $T_o$ is the temperature at the base of the sensor near its connection to the oven, $T_s$ is the temperature of the sample position of the sensor and $T_r$ is the temperature of the reference position of the sensor. $R_s$ and $R_r$ represent the thermal resistance between the base of the sensor and the sample and reference positions, respectively. $C_s$ and $C_r$ represent the thermal capacitance of the sample and reference portions of the sensor. Thermal capacitance is the product of mass and specific heat and is a measure of the heat storage capacity of a body, i.e., it is the heat capacity of the body. The heat flow rate to the sample and the reference are $q_s$ and $q_r$, respectively. It should be understood that $q_s$ and $q_r$ include heat flow to sample and reference pans. During the execution of a thermal program, the base temperature of the sensor $T_o$ follows the thermal program. The temperatures at the sample and reference positions, $T_s$ and $T_r$, lag the base temperature $T_o$ due to heat flowing to the sample and to the reference and heat which is stored within the sensor in sensor sample thermal capacitance $C_s$ and sensor reference thermal capacitance $C_r$.

Performing a heat flow balance on the sample side of the sensor yields the measured sample heat flow rate:

$$q_s = \frac{T_o - T_s}{R_s} - C_s \cdot \frac{dT_s}{d\tau}$$

which is equal to the heat flow rate through the sensor sample thermal resistance $R_s$ minus the heat stored in $C_s$. Similarly, a heat balance on the reference side of the sensor gives the measured reference heat flow rate $$q_r = \frac{T_o - T_r}{R_r} - C_r \cdot \frac{dT_r}{d\tau}$$

which is equal to the heat flow rate through sensor reference thermal resistance $R_r$ minus the heat stored in $C_r$. In the equations herein, $\tau$ represents time.

The desired quantity (the differential heat flow to the sample with respect to the reference) is the difference between the sample and reference heat flows:

$$q = q_s - q_r$$

Substituting for $q_s$ and $q_r$ yields:

$$q = \frac{T_o - T_s}{R_s} - C_s \cdot \frac{dT_s}{d\tau} - \frac{T_o - T_r}{R_r} + C_r \cdot \frac{dT_r}{d\tau}$$

Substituting the following expressions for two temperature differences in the differential scanning calorimeter, $$\Delta T = T_s - T_r$$

$$\Delta T_o = T_o - T_s$$

where $\Delta T$ is the temperature difference between the sensor sample and the reference positions and $\Delta T_o$ is the temperature difference between the sample position and a position at the base of the sensor, results in the DSC heat flow equation:

$$q = \Delta T_o \cdot \left(\frac{R_r - R_s}{R_r \cdot R_s}\right) - \frac{\Delta T}{R_r} + (C_r - C_s) \cdot \frac{dT_s}{d\tau} - C_r \cdot \frac{d\Delta T}{d\tau}$$

The DSC heat flow equation has four terms. The first term accounts for the effect of the difference between the sensor sample thermal resistance and the sensor reference thermal resistance. The second term is the conventional DSC heat flow. The third term accounts for the effect of the difference between the sensor sample thermal capacitance and the sensor reference thermal capacitance. The fourth term accounts for the effect of the difference between the heating rates of the sample and reference sides of the DSC. Conventionally, when this equation is applied to the DSC heat flow, the first and third terms are zero because $R_s$ and $R_r$ are assumed to be equal and $C_s$ and $C_r$ are also assumed to be equal. The fourth term is zero because the heating rate difference between the sample and reference is ignored.

Heat Leakage Effects

Heat leakage is defined as heat that flows between the sample or reference and the enclosure without being measured. This leakage, or unmeasured heat flow, contributes to the uncertainty of experiments in which DSCs are utilized.

Advantages that are commonly associated with using twin calorimeters in DSCs as described above include cancellation of heat leakage and temperature disturbances common to both calorimeters. If the calorimeters each contain empty sample pans, and are heated at the same rate, there should be no difference between the sensor temperatures of each enclosure. However, in practice, the two calorimeters will always generally measure a different heat flow rate. Even if the calorimeters are perfectly matched, the presence of a sample causes the sample and reference heat flow rates to be imbalanced.

When a DSC is not balanced, the leakage heat flows will not be balanced and will not cancel when the difference is taken between the measured sample and reference heat flow rates, which contributes to a measurement error in the heat flow rate. In general, the leakage heat flows are a small fraction of the measured heat flow. If the imbalance is small, the measurement error is small, as a difference between two relatively small quantities. The magnitude of the errors has been estimated for disk-type heat flux DSCs at between 1 and 5% by numerical simulation.

In principle, the uncertainty can be reduced by calibration of the heat flow rate. However, experimental conditions that are different from the calibration conditions will cause uncertainty due to heat leakage to increase. Differences in sample heat capacity and differences in the transitions within a sample are the primary differences between calibration and experimental conditions, because the experimental sample in general will have a different heat capacity from the calibrant and will have different transitions.

A manifestation of the effect of heat leakage that is well known in differential scanning calorimetry is the difference between heat flow calibration and peak area calibration. In heat flow calibration, a sample having known specific heat capacity, such as sapphire, is heated at a constant heating rate and the heat flow rate is measured. Heat capacity of the sample is obtained by dividing the heat flow rate signal by the heating rate, giving the measured heat capacity. The ratio of the actual value to the measured value gives the heat flow calibration factor for the range of temperatures of the experiment. It is applied to the results of subsequent experiments to improve the accuracy of the heat flow measurement. In peak area calibration, the sample is a material with a transition whose enthalpy is well known and highly repeatable, such as the melt of a pure metal like indium. A calibration experiment is performed and the area of the resulting heat flow rate peak is measured by integrating the heat flow signal versus time over an appropriate baseline. The area of the peak provides the measured enthalpy of the transition. The ratio of the measured enthalpy to the actual enthalpy is the peak area calibration factor.

In principle, at the temperature of the transition, the peak area and the heat flow calibration factors should be identical, or very nearly so, but in general the agreement is rather poor. The reason for this disagreement is the large temperature imbalance created by the transition and the attendant increase in sample heat leakage due to the imbalance. For example, when calibrating with a typical indium sample of 5 mg at 10° C./min, the temperature difference between the sample and the reference before the melt is of the order of only a few tenths of 1° C., but that increases to 1° C. or more at the peak of the transition. Thus, the temperatures of the sample and reference calorimeters are very far from being identical, the twin principle is severely violated, and the leakage heat flows will be much different and will not cancel each other out.

Another example of the effect of heat leakage is the well known effect of thermal conductivity of the purge gas on DSC cell calibration. In either heat flow rate or peak area calibration, it is well known that changing the purge gas causes both the peak area and the heat flow rate calibration to change. In the absence of heat leakage, both the heat flow rate calibration and peak area calibration would depend only upon thermal resistance of the calorimeters and would be independent of the purge gas used.

SUMMARY OF THE INVENTION

The present invention is a method and system for calculating a heat flow to a sample in a differential scanning calorimeter (DSC). The DSC has a sensor within an enclosure comprising an absolute temperature measurement detector for measuring the temperature of a base position on the sensor, a first differential temperature detector for measuring the temperature difference between a sample position and the base position, and a second differential temperature detector for measuring the temperature difference between a reference position and a sample position. Thermal resistances and heat capacities of the DSC are calibrated. The DSC is operated, and the heat flow to the sample is calculated using a method that includes the leakage heat flows.

The present invention is also a method and system for calculating heat flow in a differential scanning calorimeter having an independent sample measuring section and an independent reference measuring section. The heat flow rate for the sample being analyzed is determined using the measured quantities in a method that accounts for sample pan heat flow, reference pan heat flow, and heat leakage. The heat flow to a sample in the sample pan is measured in a measuring section and the heat flow to a reference is measured in a reference measuring section.

In a preferred embodiment, the present invention comprises a two step method for calibrating thermal resistances and heat capacities of a differential scanning calorimeter (DSC) having sample and reference calorimeters. in the first step, the DSC is operated empty, at a constant heating rate. A correction factor for leakage heat flow is applied to the time constants of the two calorimeters. Effective time constants are determined for the sample and reference calorimeters, accounting for heat leakage.

In the second calibration step, the DSC is operated with known calibration samples placed without pans on both of the sample and reference calorimeters of the DSC. The heat capacity is determined for each of the sample and reference sensors, accounting for heat leakage, and the sample and reference thermal resistances are calculated using the time constants from the first step and the respective heat capacities.

DETAILED DESCRIPTION OF THE INVENTION

In performing conventional differential scanning calorimetry experiments, it is assumed that the temperature difference between a sample and reference is proportional to the heat flow to the sample. However, the temperature difference is also influenced by the heat capacity of the pan, the sensing apparatus, and resistances to heat flow within certain components of the DSC. Therefore, as described in the other patents and pending applications that are incorporated by reference, methods can be performed for compensating for these effects through calibration and calculation to increase the accuracy of measurements in DSC experiments. Although these methods and systems significantly improve the instrument baseline heat flow rate, sensitivity and resolution, there has remained a problem that such measurements do not account for heat leakage. The following provides a description of a method and system for further improving the accuracy of the measurement of heat flow rates in a DSC by including the leakage heat flows in calculations of sample heat flow rate from measured signals.

Figure 1:
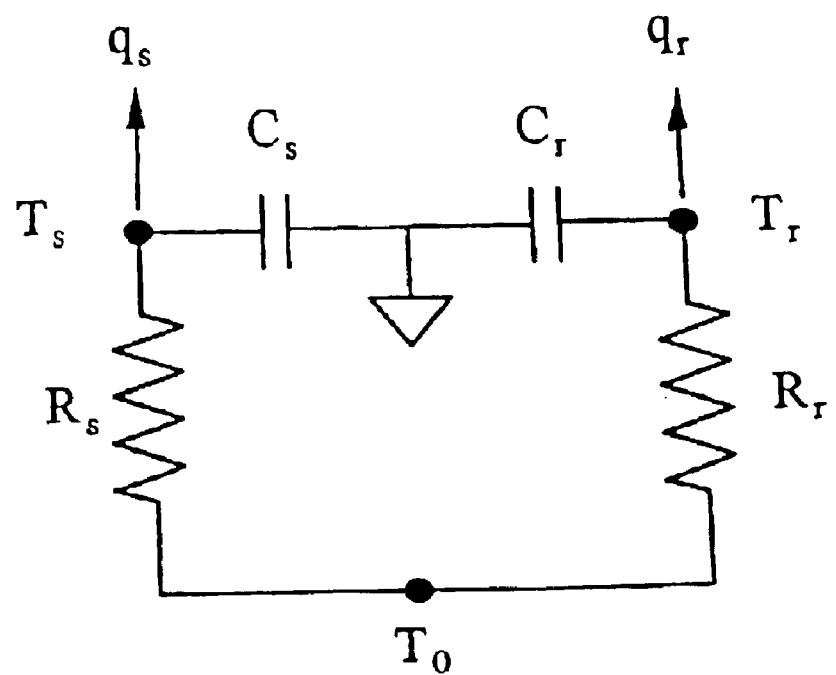
FIG. 1 is a known thermal network model of a DSC, including thermal resistances between the base of the sensor and the sample and reference positions, and thermal capacitances of the sample and reference portions of the sensor.
Figure 2:
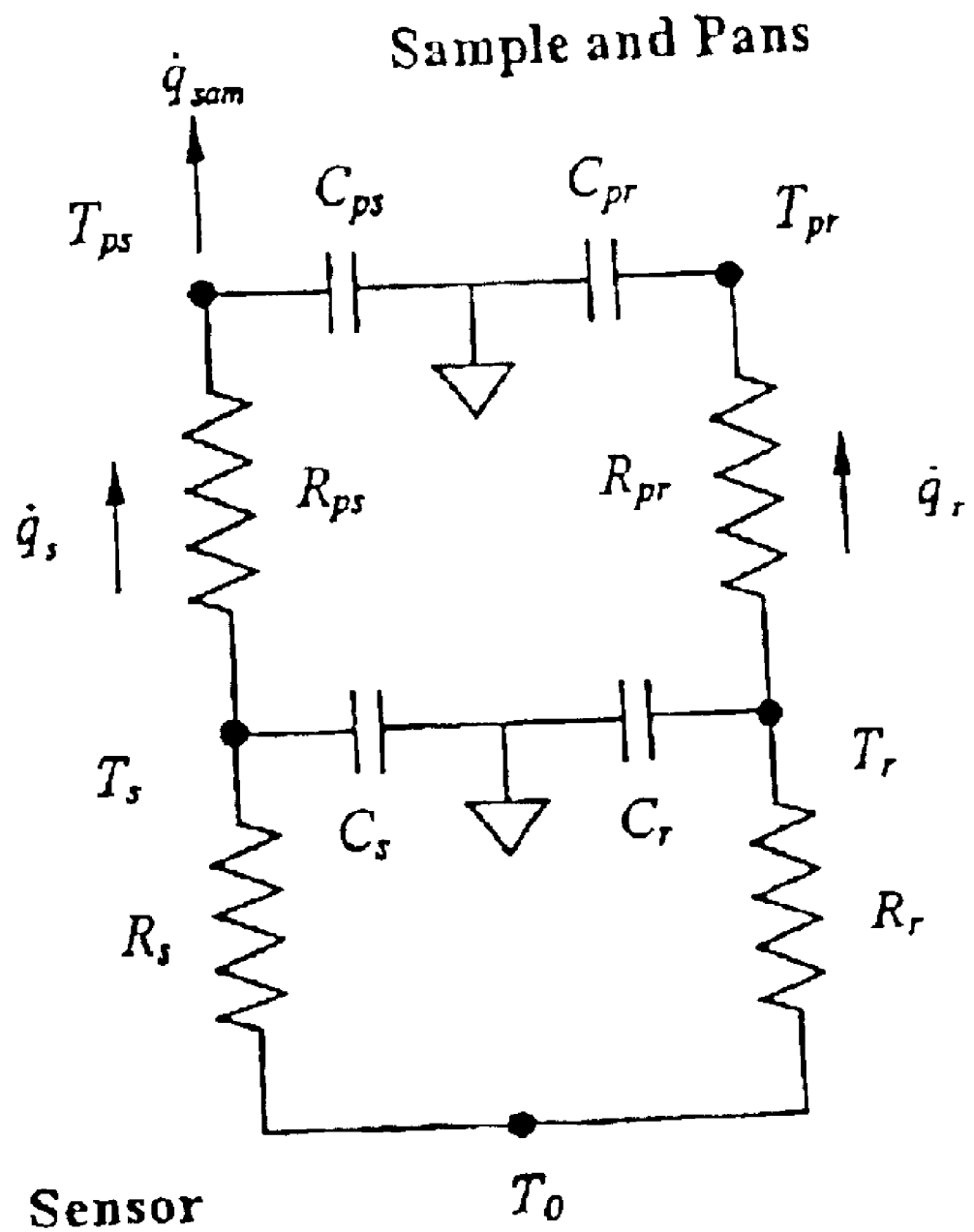
FIG. 2 is a thermal network model of a DSC, additionally including pan thermal resistances and pan thermal capacitances.

DSC Heat Flow Rate Measurement Including Sensor Asymmetry and the Effects of the Sample and Reference Pans As noted in the Background with reference to FIG. 1, the measured sample and reference heat flows $q_s$ and $q_r$ include the heat flow to the sample and reference and to their pans. FIG. 2 is a thermal network model of a DSC including thermal resistances and thermal capacitances for the reference and sample pans. $T_{ps}$ is the temperature of the sample pan and $T_{pr}$ is the temperature of the reference pan, which is assumed to be empty. $R_{ps}$ and $R_{pr}$ represent the thermal contact resistances between the pans and their respective calorimeters, and $C_{ps}$ and $C_{pr}$ represent the pan thermal capacitances. Thus, the heat flow rate to the sample pan is:

$$q_{ps} = m_{ps} \cdot c_{pan} \cdot \frac{dT_{ps}}{d\tau}$$

And the measured reference heat flow rate is just that of the empty reference pan:

$$q_r = m_{pr} \cdot c_{pan} \cdot \frac{dT_{pr}}{d\tau}$$

Where $m_{ps}$ and $m_{pr}$ are the masses of the sample and reference pans, $c_{pan}$ is the specific heat of the pan material.

Perform a heat balance on the sample pan, substitute for the sample pan heat flow and solve for the sample heat flow, giving:

$$q_{sam} = q_s - m_{ps} \cdot c_{pan} \cdot \frac{dT_{ps}}{d\tau}$$

Solve the reference heat flow equation for the pan specific heat and substitute the resulting equation for pan specific heat into the sample heat flow equation:

$$q_{sam} = q_s - q_r \cdot \frac{m_{ps}}{m_{pr}} \cdot \frac{\frac{dT_{ps}}{d\tau}}{\frac{dT_{pr}}{d\tau}}$$

This equation gives the actual sample heat flow, accounting for the sample and reference pan heat flow rates. The second term on the right hand side is seen to be the reference heat flow rate multiplied by the ratio of the sample and reference pan masses and by the ratio of the sample and reference pan heating rates. It accounts for the fact that during a transition, or during a modulated DSC experiment, the sample pan heats at a different rate than the reference pan because of the sample heat flow.

When the sample heating rate is different from the reference heating rate, the fraction of reference heat flow subtracted from the sample heat flow is greater or lesser, depending upon whether the sample pan heating rate is greater or lesser than that of the reference pan. Because the reference heat flow is just the reference pan heat flow, this equation accounts for differences between sample and reference pan heating rates. For example, during a melt in a DSC, the heating rate of the sample pan falls below the programmed rate, while the reference pan continues to heat at the programmed rate. In a conventional DSC the reference heat flow rate being subtracted from the sample heat flow rate is for a pan heating at the programmed rate. Thus, during the melt, the reference heat flow rate being subtracted from the sample heat flow rate is too large and the resultant DSC heat flow rate signal is too small. During the baseline return, the sample pan is heating faster than the reference pan and the reference heat flow rate being subtracted from the sample heat flow rate is too small and as a consequence, the DSC heat flow rate signal is too large.

To use the true sample heat flow equation requires that the sample and reference pan temperatures be known so that their derivatives may be taken. Unfortunately, there is no way to measure the pan temperatures directly. However, the pan temperatures can be calculated from the temperature and heat flow signals as follows.

The equations for heat flow between the sensor and the sample and reference pans are:

$$q_s = \frac{T_s - T_{ps}}{R_{ps}} \quad q_r = \frac{T_r - T_{pr}}{R_{pr}}$$

Solving for the pan temperatures:

$$T_{ps} = T_s - q_s R_{ps} \quad T_{pr} = T_r - q_r R_{pr}$$

Using these equations, pan temperatures and sample heat flows can be calculated from the measured signals.

The pan thermal resistances $R_{ps}$ and $R_{pr}$ depend on the pan configuration, the purge gas used in the DSC and the temperature of the DSC. Several techniques for determining $R_{ps}$ and $R_{pr}$ have been developed in the past and are well known to one of ordinary skill in the art. For example, one well-known technique is to measure the slope of the onset of a metal melt.

A preferred semi-empirical method for determining $R_{ps}$ and $R_{pr}$ is to use a model equation for heat exchange between the sample and reference pans and the DSC sensor. Because when two nominally flat surfaces are brought into contact, they only make contact over a small fraction of the projected area of contact (because the surfaces are not perfectly flat), heat exchange could occur in principle through three parallel paths: by direct solid heat conduction through the asperities of the two surfaces in contact, by convection or conduction through the interstitial gas between the surfaces and by radiation between the two surfaces. However, except in the case of extremely high heat flux and a large temperature difference between the two surfaces, radiation is insignificant, and the dominant heat exchange through the gas is by conduction. In DSC, the heat flux and the resulting temperature difference between a pan and the DSC is small and the thermal contact resistance between the surfaces can be modeled by heat conduction through two series connected solid conductors (representing each of the surfaces) in parallel with heat conduction through the gas. Using these assumptions to model the DSC pan/sensor heat exchange, the model equation for the DSC pan contact resistance is:

$$R(T) = \frac{1}{\frac{\alpha_P \cdot k_P(T) \cdot \alpha_S \cdot k_S(T)}{\alpha_P \cdot k_P(T) + \alpha_S \cdot k_S(T)} + \alpha_G \cdot k_G(T)}$$

Where, R(T) is the contact resistance as a function of temperature; $k_p(T)$, $k_s(T)$, $k_g(T)$ are thermal conductivities of the pan, sensor and gas; $\alpha_p$, $\alpha_s$ and $\alpha_g$ are geometric factors for the pan, sensor and gas. The geometric factors have the dimension of length, they may be thought of as the ratio of the area normal to the heat flow to the length of the heat conduction path. Thermal conductivities of the sensor, pan and gas are known.

The geometric factors are determined empirically as follows. The contact resistance between the pan and the sample may be measured using MDSC with average heating rate equal to zero. A sample of known heat capacity is loaded into a pan and placed on the sample position of the DSC, and the temperature is modulated sinusoidally at fixed amplitude about a given temperature. Assuming the sample and pan temperatures are the same, a two-temperature model of the DSC may be solved to find the time constant of the pan and sample.

$$\tau_s = \frac{-b_s \pm \sqrt{b_s^2 - 4a_s c_s}}{2a_s}$$

where:

$a_s = \bar{T}_s^2 \cdot (\omega^4 \cdot (C_s R_s)^2 + \omega^2) - \omega^2 \cdot \bar{T}_0^2$ $b_s = 2\bar{T}_s^2 \cdot \omega^2 \cdot C_{ss} \cdot R_s$ $c_s = \bar{T}_s^2 \cdot [1 + \omega^2 \cdot ((C_s R_s)^2 + (C_{ss} R_s)^2 + 2 C_s C_{ss} R_s^2)] - \bar{T}_0^2$ $$R_{ps} = \frac{\tau_s}{C_{ss}}$$

Where temperature with an over bar means the modulated temperature amplitude, obtained by the MDSC temperature deconvolution algorithm (as described in U.S. Pat. No. 5,224,775, which is incorporated by reference herein), $C_{ss}$ is the combined heat capacity of the sample and the pan and $\omega$ is the circular frequency of the modulation. The assumption that sample and pan temperatures are the same is justified when the modulation period is sufficiently long (typically 60 seconds or above). A similar set of equations can be written for the reference side of the DSC, and the two contact resistances may be determined in a single experiment.

Using this method for determining the contact resistance at a variety of discrete temperatures, the model equation above may be fitted to the data to determine the geometric parameters $\alpha_p$, $\alpha_s$ and $\alpha_g$. Using a multiplicity of different samples and pans, the experiments may be repeated many times and a statistically determined average value of the contact resistance can be computed.

Figure 3:
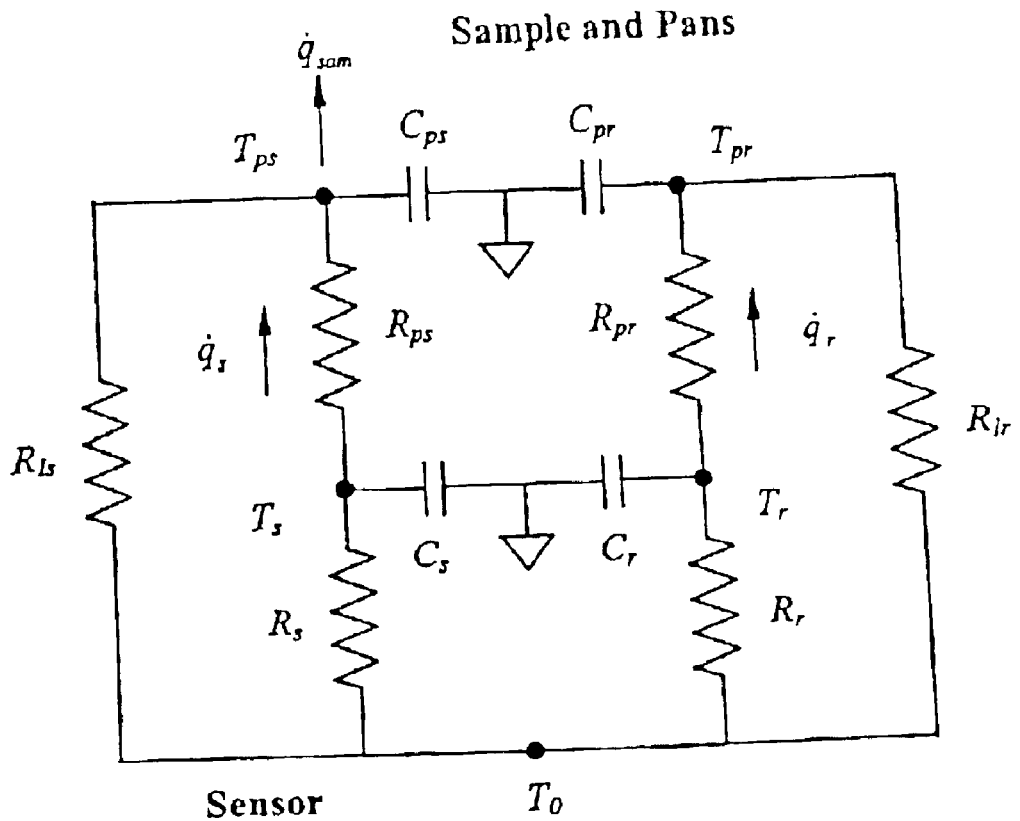
FIG. 3 is a thermal network model of a DSC, additionally accounting for heat leakage according to an embodiment of the present invention.

DSC Heat Flow Rate Measurement, Including Sensor Asymmetry, the Effects of Sample and Reference Pans and Heat Leakages FIG. 3 is a thermal network model of a DSC according to an embodiment of the present invention. As can be seen, this model includes all of the components illustrated in FIGS. 1 and 2, with the addition of the heat leakage elements. Specifically, two additional resistance elements, $R_{ls}$ and $R_{lr}$ have been added. These resistances represent leakage heat flows between the sample pan and the DSC enclosure (indicated by $T_0$) and between the reference pan and the DSC enclosure.

Addition of these two resistance elements requires modifications to the equations used to determine the actual sample heat flow. The measured sample and reference heat flows, $q_s$ and $q_r$, remain the same as described above with reference to FIG. 1.

$$\dot{q}_s = \frac{\Delta T_0}{R_s} - C_s \frac{dT_s}{dt} \quad \dot{q}_r = \frac{\Delta T_0 + \Delta T}{R_r} - C_r \left( \frac{dT_s}{dt} - \frac{d\Delta T}{dt} \right)$$

The heat exchange between the pans, sensor and DSC enclosure are considered separately. For the sample side we find, $$\dot{q}_s \left(1 + \frac{R_{ps}}{R_{ls}}\right) = \dot{q}_{sam} + m_{ps} c_{pan} \frac{dT_{ps}}{dt} - \frac{\Delta T_0}{R_{ls}}$$

For the reference side we find, $$\dot{q}_r \left(1 + \frac{R_{pr}}{R_{lr}}\right) = m_{pr} c_{pan} \frac{dT_{pr}}{dt} - \frac{\Delta T_0 + \Delta T}{R_{lr}}$$

Solving the reference heat flow equation for the pan heat capacity and eliminating it from the sample heat flow equation and solving it for $q_{sam}$:

$$\dot{q}_{sam} = \dot{q}_s\left(1 + \frac{R_{ps}}{R_{ls}}\right) + \frac{\Delta T_0}{R_{ls}} - \left(\frac{m_{ps}\frac{dT_{ps}}{dt}}{m_{pr}\frac{dT_{pr}}{dt}}\right)\left(\dot{q}_r\left(1 + \frac{R_{pr}}{R_{lr}}\right) + \frac{\Delta T_0 + \Delta T}{R_{lr}}\right)$$

Thus, it is seen that the sample heat flow equation including the heat flow leakages differs from the equation of the previous invention (i) by factors multiplying the measured heat flows, and (ii) by an additional term for both the sample and the reference sides. The factors and additional terms tend to increase the magnitude of the measured sample heat flow rate. The form of the equation makes sense intuitively, as leakage heat flows tend to decrease the measured heat flow.

The leakage heat flow consists of heat that is exchanged directly between the sample and reference pans and the DSC enclosure by the combination of radiation and heat transfer through the gas within the enclosure. The leakage thermal resistance is much larger than the pan contact thermal resistance, for example one group of researchers found that near 156° C., the leakage resistance was 784° C./watt while the pan contact resistance was 10° C./watt.

Calibration of a DSC that Measures the Heat Flow Rate Including Sensor Asymmetry and the Effects of the Sample and Reference Pans The following describes a method for calibrating thermal resistances and heat capacities of a DSC that are necessary to measure heat flow rate, for a DSC according to the thermal model of FIGS. 1 and 2. This is performed by running two separate experiments. These experiments determine the four sensor thermal parameters, $C_s$ (the sensor sample thermal capacitance), $C_r$ (the sensor reference thermal capacitance), $R_s$ (the sensor sample thermal resistance) and $R_r$ (the sensor reference thermal resistance) experimentally, and thus calibrate the heat flow sensor.

The first experiment is performed with an empty DSC cell. The DSC cell is first held at an isothermal temperature that is below the temperature range of the calibration, for a time segment sufficient to ensure complete equilibration of the sensor. The DSC cell is then heated at a constant heating rate to a temperature above the temperature range of the calibration, and then held at that temperature for another isothermal segment, for a time segment sufficient to ensure equilibration of the sensor at that temperature. This first experiment is used to calculate the sample and reference time constants as a function of temperature over the calibrated temperature range.

The measured sample and reference heat flow rates should be zero (since the DSC cell is empty). Accordingly, if $q_s$ and $q_r$ are set equal to zero in the heat balance equations for the sample and reference sides of the sensor, the time constants for the sample and reference are given by:

$$\tau_s = C_s R_s = \frac{\Delta T_0}{\left(\frac{dT_s}{d\tau}\right)}$$

and $$\tau_r = C_r R_r = \frac{\Delta T_o + \Delta T}{\frac{dT_s}{d\tau} - \frac{d\Delta T}{d\tau}}$$

respectively. These results are stored as a function of temperature.

The second experiment uses a pair of calibration samples. The calibration samples may have the same mass, or may have different masses. Preferably, the calibration samples are monolithic sapphire samples, preferably weighing 25 mg or more. Other reference materials with well-known specific heats and no transitions in the temperature range of the calibration may be used instead of sapphire (in which case Csapph would be replaced in the following equations by Cmat where Cmat is the specific heat of the other reference material).

The sample and reference heat flows from the heat balance equations are set as follows:

$$q_s = m_s \cdot C_{sapph} \cdot \frac{dT_{ss}}{d\tau}$$

$$q_r = m_r \cdot C_{sapph} \cdot \frac{dT_{rs}}{d\tau}$$

where $m_s$, $m_r$ are the masses of the sample and reference sapphires, respectively, $C_{sapph}$ is the specific heat of sapphire and $T_{ss}$ and $T_{rs}$ are the temperatures of the sample and reference sapphire.

Assume:

$$\frac{dT_{ss}}{d\tau} = \frac{dT_s}{d\tau} \quad \text{and} \quad \frac{dT_{rs}}{d\tau} = \frac{dT_r}{d\tau}$$

Substituting for $q_s$ and $\tau_s$ in the sample heat balance equation and solving for the sensor sample thermal capacitance $C_s$:

$$C_s = \frac{m_s \cdot Csapph}{\frac{\Delta T_o}{\left(\frac{dT_s}{d\tau}\right) \cdot \tau_s} - 1}$$

Substituting for $q_r$ and $\tau_r$ in the reference heat balance equation and solving for the sensor reference thermal capacitance $C_r$:

$$C_r = \frac{m_r \cdot C_{sapph}}{\frac{\Delta T_o + \Delta T}{\left(\frac{dT_s}{d\tau} - \frac{d\Delta T}{d\tau}\right) \cdot \tau_r} - 1}$$

The results from the second experiment using sapphire (or another well-known calibration material) and using the time constants for a DSC cell obtained in the first experiment are used as shown above to calculate the sample and reference sensor heat capacities as a function of temperature. Finally, the sensor sample and reference thermal resistances are calculated from the time constants and the sensor thermal capacitances:

$$R_s = \frac{\tau_s}{C_s} \quad \text{and} \quad R_r = \frac{\tau_r}{C_r}$$

Calibration of a DSC that Measures the Heat Flow Rate Including Sensor Asymmetry, the Effects of the Sample and Reference Pans and Heat Leakages In accordance with an embodiment of the present invention, the calibration procedure described above for calibrating thermal resistances and heat capacities of a DSC can be modified to include the heat leakages.

Figure 4:
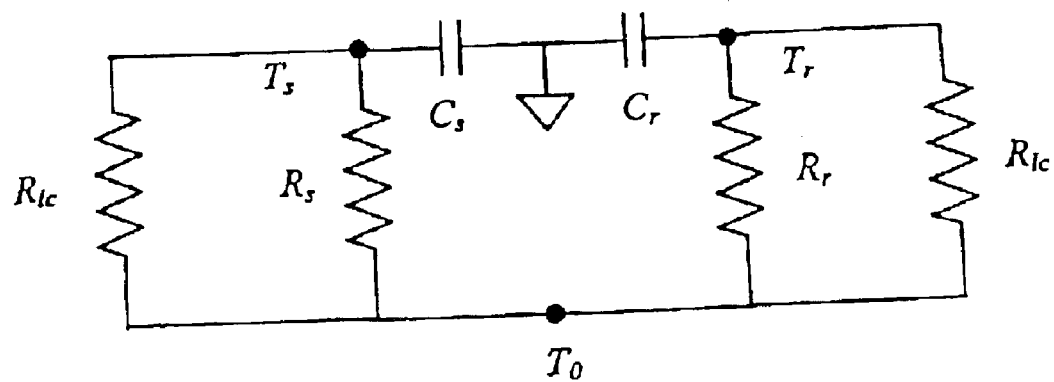
FIG. 4 is a thermal network model of an empty DSC including heat flow leakages, according to an embodiment of the present invention.

The first of the two calibration experiments involves running the DSC empty at a constant heating rate, but because of leakage heat flow, the measured heat flow is not zero. In the model of the empty DSC shown in FIG. 4, the leakage thermal resistances $R_{lc}$ are added in parallel to the measuring thermal resistances $R_s$ and $R_r$. The effect of the addition of these new resistances is to decrease the effective resistance of the measuring resistances $R_s$ and $R_r$. The effective resistances replace the measuring resistances in the first calibration equations:

$$R'_s = \frac{R_s R_{lc}}{R_s + R_{lc}} \qquad R'_r = \frac{R_r R_{lc}}{R_r + R_{lc}}$$

The effective time constant of the two calorimeters can be found as before:

$$\tau'_s = C_s R'_s = \frac{\Delta T}{\frac{dT_s}{dt}} \qquad \tau'_r = C_r R'_r = \frac{\Delta T_0 - \Delta T}{\frac{dT_s}{dt} - \frac{d\Delta T}{dt}}$$

The leakage thermal resistances are assumed to be known, while the magnitude of the measuring resistances is generally known to within 5% before calibration. This allows a correction factor to be applied to the time constant as follows. The ratio of the measuring thermal resistance to the effective measuring resistance is:

$$K = \frac{R_m}{R'_m} = \frac{R_m + R_{lc}}{R_{lc}}$$

This time constant correction factor varies with temperature and with the type of purge gas used. Also, in this equation the subscript m is a generic subscript representing either the subscript s or the subscript r. The calorimeter time constants corrected for leakage heat flow are:

$$\tau_s = K\tau'_s, \tau_r = K\tau'_r$$

Because the leakage thermal resistance is much larger than the sensor thermal resistances, the time constant correction factor is a number that is close to unity and is fairly insensitive to typical variations in the sensor thermal resistances ($R_s$ and $R_r$). Thus, the use of a standard value of the correction factor results in relatively small uncertainty. However even that uncertainty may be reduced by performing an iterative analysis of the calculation data where the sensor thermal resistances are calculated and used to calculate a new correction factor which is used to calculate yet another value of the sensor thermal resistances, iteration continues until the changes in sensor thermal resistance diminish sufficiently.

The second calibration experiment is identical to the first, except that calibration sample without pans are placed on both the sample and the reference sides of the calorimeter. The sample heat flow equation given above with reference to FIG. 3 is used with the sample heat flow rate set equal to zero, the heat capacity of the calibration sample replaces that of the pan, and the calibration sample temperature replaces that of the pan.

$$C_{ss}\frac{dT_{ss}}{dt} = \dot{q}_s\left(1 + \frac{R_{ss}}{R_{ls}}\right) + \frac{\Delta T_0}{R_{ls}}$$

Substituting the sample heat flow measurement equation, assuming that the heating rate of the calibration sample and the sensor are the same, and solving for the sample sensor heat capacity:

$$C_s = \frac{C_{ss}\frac{dT_s}{dt} - \frac{\Delta T_0}{R_{ls}}}{\left(\frac{\Delta T_0}{\tau_s} - \frac{dT_s}{dt}\right)\left(1 + \frac{R_{ss}}{R_{ls}}\right)}$$

And similarly, the reference sensor heat capacity is:

$$C_r = \frac{C_{sr}\left(\frac{dT_s}{dt} - \frac{d\Delta T}{dt}\right) - \frac{\Delta T_0 + \Delta T}{R_{lr}}}{\left(\frac{\Delta T_0 + \Delta T}{\tau_r} - \frac{dT_s}{dt} + \frac{d\Delta T}{dt}\right)\left(1 + \frac{R_{sr}}{R_{lr}}\right)}$$

where $C_{ss}$ and $C_{sr}$ are the heat capacities of the sample and reference calibration samples respectively, and $R_{ls}$ and $R_{lr}$ are the leakage thermal resistances and $R_{ss}$ and $R_{sr}$ are the contact thermal resistances of the sample and reference calibration samples, respectively.

The sample and reference thermal resistances are then calculated from the time constants and thermal resistances:

$$R_s = \frac{\tau_s}{C_s} \qquad R_r = \frac{\tau_r}{C_r}$$

With the calibration complete, heat flow measurements may be made that includes the leakage heat flows.

Determining Leakage Thermal Resistances

To implement the measurement and calibration methods described above requires that the leakage thermal resistances be known. There are in fact three different leakage thermal resistances required to perform a calibration of the instrument and the subsequent measurement. The first is the leakage resistance of an empty DSC cell as used in the first step of the calibration; it represents the combination of radiation and gas heat transfer between the DSC sensor and the enclosure. The second is the leakage thermal resistance between the calibration samples and the enclosure; it represents the combination of radiation and gas heat transfer between each calibration sample and the enclosure. The third is the leakage thermal resistance between a sample pan and the DSC enclosure; it represents the combination of radiation and gas heat transfer between each pan and the enclosure. The values of leakage thermal resistances can be computed using Finite Element Analysis of the DSC cell including the interior of the enclosure, the sample pans and the sensor.

Finite element modeling is a well-established engineering tool wherein a component of arbitrary shape is considered to be comprised of a series of small elements of finite size. Using commercially or publicly available software, a set of equations is devised that relates the flow of heat through each of the elements to temperatures at the element's nodes. The resulting set of equations is solved to find the temperature distribution within the model from which the heat flow rates between surfaces of interest may be calculated. Simulated experiments are then run to determine the heat flows and to use the temperature differences and the rates of heat flowing to calculate equivalent leakage thermal resistances. Finite element analysis can be used to create values for the DSC leakage thermal resistances at different temperatures, to be coded into the instrument as software. A look-up table can then be used to identify a correct value of resistance for a particular temperature. The values change at different temperatures because the thermal conductivity of all of the materials that the DSC is constructed of changes, such that they are functions of temperature. These results will be used to create tables of leakage resistances as a function of temperature for empty DSC cells for each pan type and using selected purge gases. Radiation and gas conduction will both be included.

Figure 5:
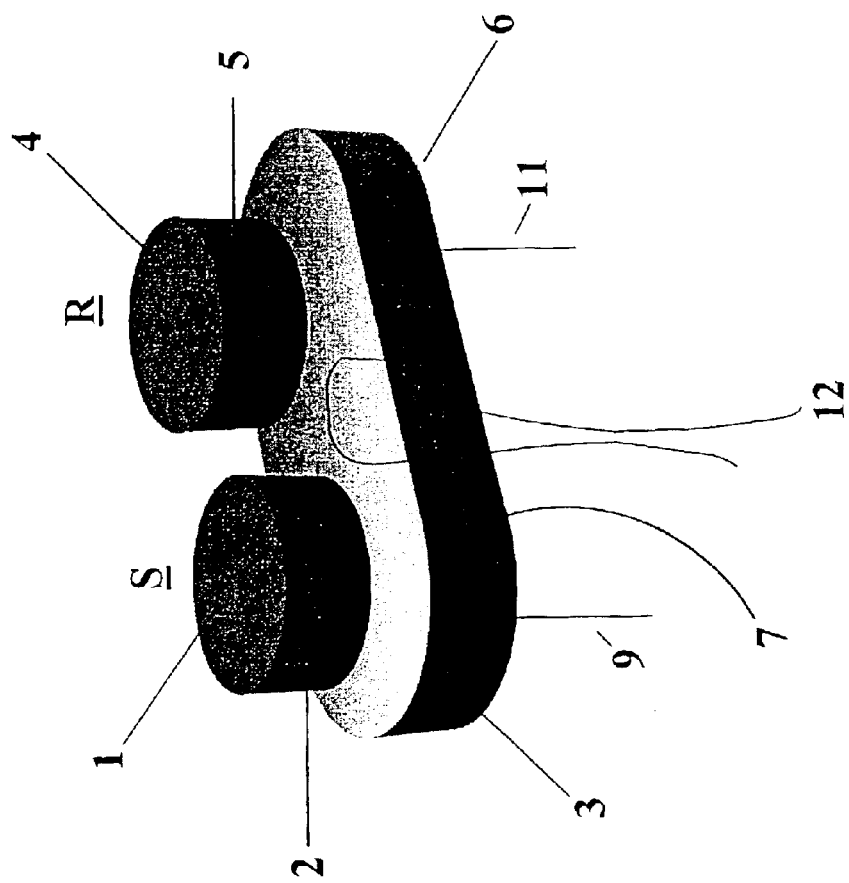
FIG. 5 is a schematic diagram of a heat flux DSC sensor according to the present invention.

Apparatus embodying the present invention are shown schematically in FIGS. 5–8. FIG. 5 shows sample platform 1 and reference platform 4 mounted on thin circular tubes 2 and 5, respectively. These are mounted on base 3. The platforms, tubes and base are integral part of sensor body 6, which is typically made of constantan, the negative element of a Type E thermocouple. The thin wall tube portions 2 and 5 of the sensor body are the principal contributors to the thermal resistances $R_s$ and $R_r$ of the DSC sensor. The underside 7 of the base is a flat surface, which is the mounting surface used to install the sensor in the DSC oven. FIG. 5 also shows thermocouple leads 9, 11 and 12.

Figure 6:
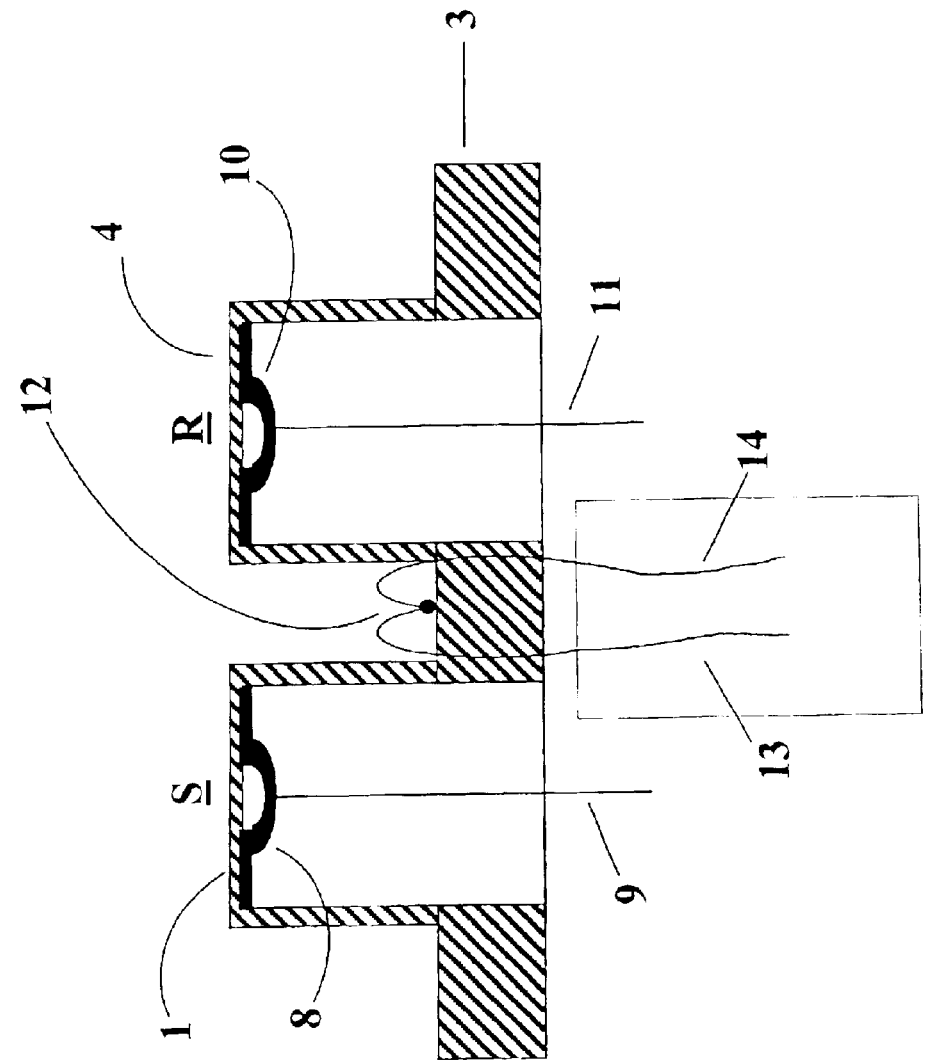
FIG. 6 is a cross-sectional schematic diagram of the heat flux DSC sensor shown in FIG. 5.

FIG. 6 is a schematic diagram of a cross sectional view through an exemplary DSC sensor, taken at a plane perpendicular to and passing through the centers of the sample and reference platforms. In addition to the components identified above with reference to FIG. 5, FIG. 6 also shows sample area temperature detector 8 and reference area temperature detector 10, which are welded to the underside of their respective platforms, and thermocouple leads 9 and 11 (typically, chromel), lead wire 13 (chromel) and lead wire 14 (constantan).

Figure 7:
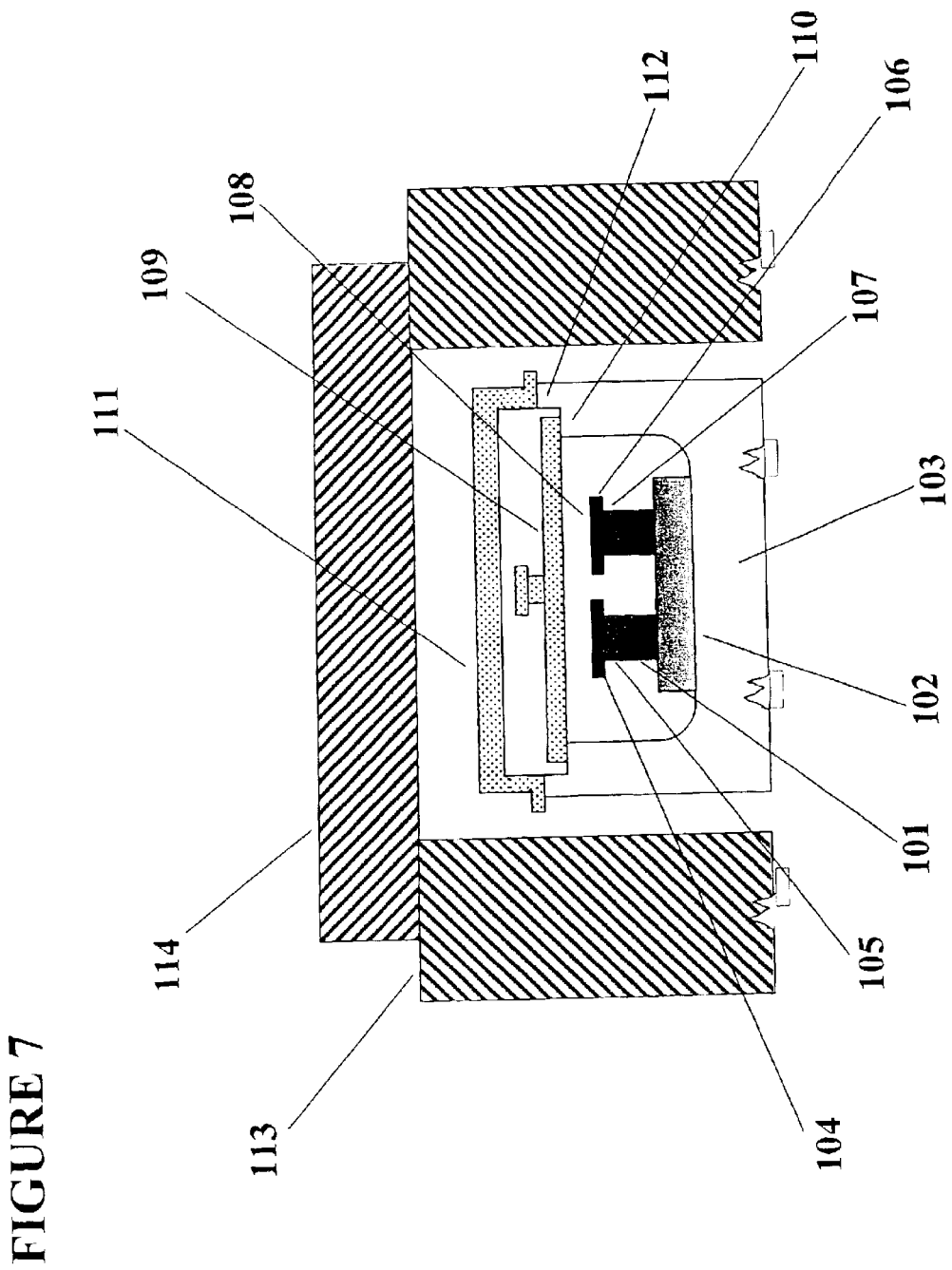
FIG. 7 is a schematic diagram of a cross-section of a heat flux DSC cell assembly.

FIG. 7 is a schematic diagram of a cross section through the upper portion of an exemplary DSC cell assembly. The lower portion is omitted for clarity. The DSC sensor 101 is mounted to the lower surface 102 of the body 103 of the DSC enclosure. The sample in pan 104 and the reference (if used) in pan 106 are placed on their respective positions 105 and 107. The cavity 108 of the DSC enclosure is closed by inner lid 109. Inner lid 109 rests on surface 110 of the enclosure body 103. Body 103 is typically fabricated from a high-conductivity material, such as silver. Outer lid 111 rests on body 103 on surface 112, such that inner lid 109 and outer lid 111 are not in contact with each other. The assembly also comprises a thermal insulation enclosure, which comprises body 113 and removable lid 114.

Figure 8:
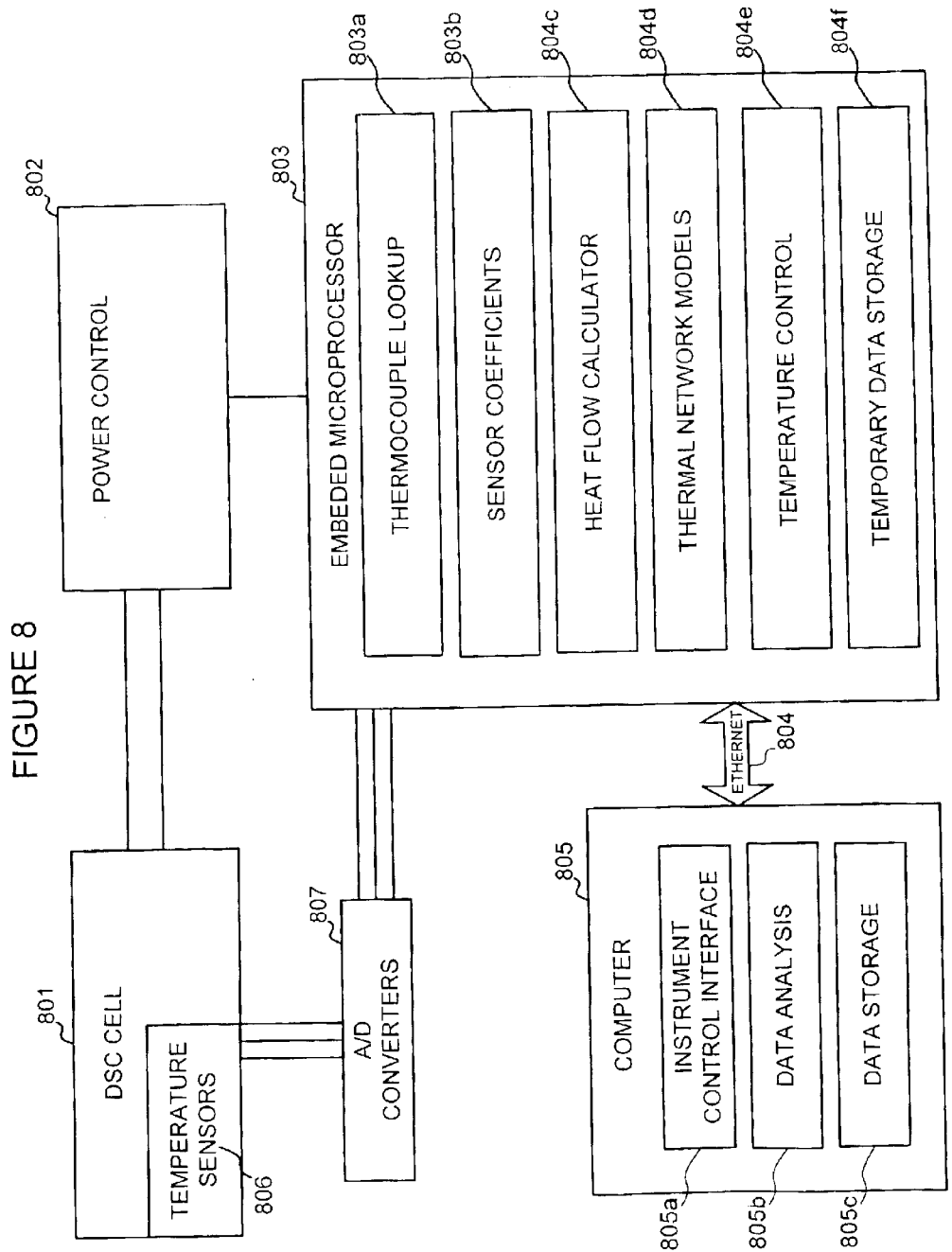
FIG. 8 is a schematic diagram of a system embodying the present invention.

FIG. 8 shows an exemplary DSC system, including the DSC cell 801, temperature sensors 806, A/D converters 807, power control module 802, embedded microprocessor 803 and computer 805. In this example, embeded microprocessor 803 comprises a thermocouple lookup 803a, sensor coefficients 803b, heat flow calculator 803c, thermal network models 804d, temperature control 804e and temporary data storage 804f. Computer 805 comprises instrument control interface 805a, data analysis module 805b and data storage 805c. FIG. 8 is only exemplary, and one or more of the components of embedded microprocessor 803 could instead reside on computer 805, and vice-versa. Computer 805 and microprocessor 803 communicate over, for example, ethernet connection 804. Also, microprocessor 803 and computer 805 could represent more than one microprocessor or computer, respectively.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

List of Symbols

The following symbols are all defined above, but are listed here for convenience when reading and applying the claims:

q is the differential heat flow to the sample with respect to the reference;
$q_s$ is the measured sample heat flow;
$q_r$ is the measured reference heat flow;
$T_o$ is the temperature of the base of the sensor;
$T_s$ is the temperature of the sample position;
$T_r$ is the temperature of the reference position;
$C_s$ is the sensor sample thermal capacitance;
$C_r$ is the sensor reference thermal capacitance;
$R_s$ is the sensor sample thermal resistance;
$R_r$ is the sensor reference thermal resistance;
$\tau$ represents time;
$\Delta T$ is the temperature difference between the sample and reference positions;
$\Delta T_o$ is the temperature difference between the sample position and the position of the base of the sensor;
$T_{ps}$ is the temperature of the sample pan;
$T_{pr}$ is the temperature of the reference pan;
$R_{ps}$ is the thermal contact resistance between the sample pan and the sample calorimeter;
$R_{pr}$ is the thermal contact resistance between the reference pan and the reference calorimeter;
$C_{ps}$ is the sample pan thermal capacitance;
$C_{pr}$ is the reference pan thermal capacitance;
$M_{ps}$ is the mass of the sample pan;
$M_{pr}$ is the mass of the reference pan;
$c_{pan}$ is the specific heat of the pan material;
$q_{sam}$ is the actual sample heat flow;
$\alpha_p$ is the pan geometric factor;
$\alpha_s$ is the sensor geometric factor;
$\alpha_g$ is the gas geometric factor;
$k_p$ is the pan thermal conductivity;
$k_s$ is the sensor thermal conductivity;
$k_g$ is the gas thermal conductivity;
$\tau_s$ is the time constant of the pan and sample;
$\tau_r$ is the time constant of the pan and reference;
$\omega$ is the frequency of the sinusoidal modulation;
$R_{ls}$ is the resistance due to leakage heat flow between the sample pan and the DSC enclosure;
$R_{lr}$ is the resistance due to leakage heat flow between the reference pan and the DSC enclosure;
$C_{sapph}$ is the specific heat of sapphire;
$T_{ss}$ is the temperature of the sample sapphire;
$T_{rs}$ is the temperature of the reference sapphire;
$R_s'$ is the effective sample resistance;
$R_r'$ is the effective reference resistance;
$\tau_s'$ is the effective sample time constant;
$\tau_r'$ is the effective reference time constant;
K is the correction factor that accounts for the leakage heat flow;

$C_{ss}$ is the heat capacity of the sample calibration sample;
$C_{sr}$ is the heat capacity of the reference calibration sample;
$R_{ss}$ is the contact thermal resistance of the sample calibration sample;
$R_{sr}$ is the contact thermal resistance of the reference calibration sample.

What is claimed is:

1. A method for calculating a heat flow to a sample in a differential scanning calorimeter (DSC) having a sensor within an enclosure comprising an absolute temperature measurement detector for measuring temperature of a base position on the sensor, a first differential temperature detector for measuring a temperature difference between a sample position and the base position, and a second differential temperature detector for measuring a temperature difference between a reference position and a sample position, comprising:
   calibrating measuring thermal resistances and heat capacities of the DSC, wherein heat leakages are accounted for in the calibration such that leakage thermal resistances associated with heat leakage decrease an effective resistance of the measuring thermal resistances;
   operating the DSC; and
   calculating the heat flow to the sample in accordance with the calibration of the measuring thermal resistances and heat capacities of the DSC.

2. The method of claim 1, wherein the step of calibration additionally determines a sensor sample thermal capacitance $C_s$ and a sensor reference thermal capacitance $C_r$.

3. The method of claim 1, wherein calibration is performed in an empty DSC and a first leakage resistance $R_{lc}$ is added in parallel to a measuring thermal resistance of a sample $R_s$ and a second leakage resistance $R_{lc}$ is added in parallel to a measuring thermal resistance of a reference $R_r$, thereby decreasing an effective resistance of the measuring thermal resistances.

4. The method of claim 3, wherein leakage resistance $R_{lc}$ of an empty differential scanning calorimeter cell represents a combination of at least the radiation and conduction between the sensor of the differential scanning calorimeter and the enclosure through the gas.

5. The method of claim 1, wherein calibration is performed with first and second calibration samples without pans placed on respective sample and reference sides of the DSC, and a leakage thermal resistance $R_{lr}$ between the first calibration sample and an enclosure is added in parallel to a measuring thermal resistance of the sample calorimeter, and a leakage thermal resistance $R_{ls}$ between the second calibration sample and an enclosure is added in parallel to a measuring thermal resistance of the reference calorimeter.

6. The method of claim 5, wherein the leakage thermal resistance $R_{lr}$ between each calibration sample and respective enclosure represents a combination of at least radiation and conduction between the calibration sample and the respective enclosure through the gas.

7. The method of claim 1, wherein the leakage thermal resistances associated with heat leakage are calculated prior to performing calibration.

8. The method of claim 7, wherein the leakage thermal resistances are computed using finite element analysis of the DSC, including an analysis of the interior of the enclosure, sample pans, and the sensor.

9. The method of claim 8, wherein leakage thermal resistances are calculated at different temperatures.

10. The method of claim 8, wherein leakage thermal resistances are calculated for different pan types.

11. The method of claim 8, wherein leakage thermal resistances are calculated using any combination of (i) different purge gases in the DSC, (ii) unpurged gas within the cell, and (iii) a vacuum.

12. The method of claim 1, wherein the step of calculating the heat flow to the sample is determined according to:

$$\dot{q}_{sam} = \dot{q}_s\left(1 + \frac{R_{ps}}{R_{ls}}\right) + \frac{\Delta T_0}{R_{ls}} - \left(\frac{m_{ps}\frac{dT_{ps}}{dt}}{m_{pr}\frac{dT_{pr}}{dt}}\right)\left(\dot{q}_r\left(1 + \frac{R_{pr}}{R_{lr}}\right) + \frac{\Delta T_0 + \Delta T}{R_{lr}}\right),$$

wherein $q_s$ is a measured sample heat flow, $q_r$ is a measured reference heat flow, $R_{ps}$ is a thermal resistance between a sample pan and a sensor, $R_{pr}$ is a thermal resistance between a reference pan and the sensor, $R_{ls}$ is a thermal resistance for heat leakage for a sample pan, $R_{lr}$ is a thermal resistance for heat leakage for a reference pan, $\Delta T_o$ is a temperature difference between a sample position and a position of the base of the sensor, $\Delta T$ is a temperature difference between the sample and reference positions, $dT_{ps}$ is a change in temperature in the sample pan, $dT_{pr}$ is a change in temperature in the reference pan, $m_{ps}$ is a mass of the sample pan, and $m_{pr}$ is a mass of the reference pan.

13. A method for calculating heat flow in a differential scanning calorimeter having an independent sample measuring section and an independent reference measuring section, comprising:
   calibrating the differential scanning calorimeter; accounting for sample pan heat flow, reference pan heat flow, and heat leakage, wherein heat leakages are accounted for in the calibration such that leakage thermal resistances associated with heat leakage decrease an effective resistance of measuring thermal resistances; and
   measuring a heat flow to a sample and a respective sample pan in the sample measuring section and measuring a heat flow to a reference pan in the reference measuring section, wherein heat flow is calculated based upon the measured heat flow to the sample and sample pan and the measured heat flow to the reference pan, in accordance with the calibration of the differential scanning calorimeter.

14. The method of claim 13, wherein the heat flow to the sample is calculated according to:

$$\dot{q}_{sam} = \dot{q}_s\left(1 + \frac{R_{ps}}{R_{ls}}\right) + \frac{\Delta T_0}{R_{ls}} - \left(\frac{m_{ps}\frac{dT_{ps}}{dt}}{m_{pr}\frac{dT_{pr}}{dt}}\right)\left(\dot{q}_r\left(1 + \frac{R_{pr}}{R_{lr}}\right) + \frac{\Delta T_0 + \Delta T}{R_{lr}}\right),$$

wherein $q_s$ is a measured sample heat flow, $q_r$ is a measured reference heat flow, $R_{ps}$ is a thermal resistance between a sample pan and a sensor, $R_{pr}$ is a thermal resistance between a reference pan and the sensor, $R_{ls}$ is a thermal resistance for heat leakage for a sample pan, $R_{lr}$ is a thermal resistance for heat leakage for a reference pan, $\Delta T_o$ is a temperature difference between a sample position and a position of the base of the sensor, $\Delta T$ is a temperature difference between the sample and reference positions, $dT_{ps}$ is a change in temperature in the sample pan, $dT_{pr}$ is a change in temperature in the reference pan, $m_{ps}$ is a mass of the sample pan, and $m_{pr}$ is a mass of the reference pan.

15. A method of calibrating thermal resistances and heat capacities of a differential scanning calorimeter (DSC) for measuring heat flow and having sample and reference calorimeters, comprising:

operating the DSC empty, without pans or samples, at a constant heating rate;

applying a correction factor for leakage heat flow to a time constant of the sample and reference calorimeters, determining effective time constants for the sample and reference calorimeters, accounting for heat leakage;

operating the DSC with calibration samples without pans on a sample position and on a reference position; and calculating sample and reference thermal resistances in accordance with effective time constants associated with the two operations of the DSC.

16. The method of claim 15, further comprising the steps of:

operating the DSC with known calibration samples placed without pans on both of the sample and reference calorimeters of the DSC; and determining a heat capacity for each of the sample and reference calorimeters, accounting for heat leakage, wherein the sample and reference thermal resistances are calculated in accordance with effective time constants and the respective heat capacities.

17. The method of claim 15, wherein a leakage resistance $R_{lc}$ is added in parallel to a measuring thermal resistance of a sample $R_s$, thereby decreasing the effective resistance of a measuring thermal resistance $R'_s$ according to:

$$R'_s = \frac{R_s R_{lc}}{R_s + R_{lc}}.$$

18. The method of claim 17, wherein the leakage thermal resistance is calculated prior to performing calibration.

19. The method of claim 17, wherein the leakage thermal resistance is computed using finite element analysis of the DSC, including an interior of the enclosure, sample pans, and the sensor.

20. The method of claim 17, wherein the leakage thermal resistance is calculated for different pan types.

21. The method of claim 17, wherein an effective time constant $\tau'_s$ is determined by:

$$\tau'_s = C_s R'_s = \frac{\Delta T_0}{\frac{dT_s}{dt}},$$

wherein $C_s$ is a sensor thermal capacitance, $\Delta T_o$ is a temperature difference between the sample position and the position of the base of the sensor, and $dT_s$ is a change in temperature of the sample position.

22. The method of claim 15, wherein a leakage resistance $R_{lc}$ is added in parallel to a measuring thermal resistance of a reference $R_r$, thereby decreasing the effective resistance of a measuring thermal resistance $R'_r$ according to:

$$R'_r = \frac{R_r R_{lc}}{R_r + R_{lc}}.$$

23. The method of claim 22, wherein an effective time constant $\tau'_r$ is determined by:

$$\tau'_r = C_r R'_r = \frac{\Delta T_0 - \Delta T}{\frac{dT_s}{dt} - \frac{d\Delta T}{dt}},$$

wherein $C_r$ is a sensor thermal capacitance, $\Delta T_o$ is a temperature difference between the sample position and the position of the base of the sensor, and $dT_s$ is a change in temperature of the sample position.

24. The method of claim 15, wherein a correction factor K is determined according to a ratio of a measuring thermal resistance $R_m$ to an effective measuring resistance $R'_m$ reduced by a leakage resistance $R_{lc}$, according to:

$$K = \frac{R_m}{R'_m} = \frac{R_m + R_{lc}}{R_{lc}},$$

and time constants corrected for leakage heat flow are determined by the products of effective time constants and the correction factor.

25. A method of calibrating thermal resistances and heat capacities of a differential scanning calorimeter (DSC) for measuring heat flow and having sample and reference calorimeters, comprising:

operating the DSC with known calibration samples placed without pans on both of the sample and reference calorimeters of the DSC; and determining a heat capacity for each of sample and reference sensors in the respective sample and reference calorimeters, accounting for heat leakage, wherein sample and reference thermal resistances are calculated in accordance with the respective heat capacities and heat leakage is accounted for in determining the heat capacities such that leakage thermal resistances associated with heat leakage decrease an effective resistance of measuring thermal resistances.

26. The method of claim 25, further comprising the steps of:

operating the DSC empty, without pans or samples, at a constant heating rate;

applying a predetermined correction factor accounting for leakage heat flow to a time constant of the two calorimeters; and determining effective time constants for the sample and reference calorimeters, accounting for heat leakage;

wherein sample and reference thermal resistances are calculated in accordance with effective time constants and the respective heat capacities.

27. The method of claim 25, wherein a leakage thermal resistance $R_{ls}$ is added in parallel with the thermal resistance of the calibration sample $R_{ss}$, and a heat capacity of a sample sensor $C_s$ is determined according to:

$$C_s = \frac{C_{ss}\frac{dT_s}{dt} - \frac{\Delta T_0}{R_{ls}}}{\left(\frac{\Delta T_0}{\tau_s} - \frac{dT_s}{dt}\right)\left(1 + \frac{R_{ss}}{R_{ls}}\right)},$$

wherein $C_{ss}$ is a heat capacity of the calibration sample, $\Delta T_o$ is a temperature difference between the sample position and the position of the base of the sensor, and $dT_s$ is a change in temperature of the sample position.

28. The method of claim 25, wherein the sample thermal resistance is determined according to a time constant for the sample divided by the heat capacity of the sample sensor $C_s$.

29. The method of claim 22, wherein a leakage thermal resistance $R_{lr}$ is added in parallel with the thermal resistance of the reference disk $R_{sr}$, and a heat capacity of the reference sensor $C_r$ is determined according to:

$$C_r = \frac{C_{sr}\left(\dfrac{dT_s}{dt} - \dfrac{d\Delta T}{dt}\right) - \dfrac{\Delta T_0 + \Delta T}{R_{lr}}}{\left(\dfrac{\Delta T_0 + \Delta T}{\tau_r} - \dfrac{dT_s}{dt} + \dfrac{d\Delta T}{dt}\right)\left(1 + \dfrac{R_{sr}}{R_{lr}}\right)},$$

wherein $C_{sr}$ is a heat capacity of the reference calibration sample, $\Delta T_o$ is a temperature difference between the sample position and the position of the base of the sensor, and $dT_s$ is a change in temperature of the sample position.

30. The method of claim 29, wherein the reference thermal resistance is determined according to a time constant for the reference divided by the heat capacity of the reference sensor $C_r$.

31. A method for calculating a heat flow to a sample in a differential scanning calorimeter (DSC) having a sensor within an enclosure comprising a first differential temperature detector, a second differential temperature detector, and a third differential temperature detector, comprising:
  calibrating measuring thermal resistances and heat capacities of the DSC, accounting for thermal resistances associated with heat leakage, wherein heat leakages are accounted for in the calibration such that leakage thermal resistances associated with heat leakage decrease an effective resistance of measuring thermal resistances;
  operating the differential scanning calorimeter; and
  calculating the heat flow to the sample
  wherein the first differential temperature measures one of a temperature difference between a sample position and a base position, a temperature difference between a reference position and the base position, and a temperature difference between the reference position and the sample position,
  and wherein the second differential temperature detector measures a second one of the temperature difference between the sample position and the base position, the temperature difference between the reference position and the base position, and the temperature difference between the reference position and the sample position,
  and wherein the second differential temperature detector measures the third one of the temperature difference between the sample position and the base position, the temperature difference between the reference position and the base position, and the temperature difference between the reference position and the sample position.

32. The method of claim 31, wherein the step of calibration additionally determines a sensor sample thermal capacitance $C_s$ and a sensor reference thermal capacitance $C_r$.

33. The method of claim 31, wherein calibration is performed in an empty DSC and a first leakage resistance $R_{lc}$ is added in parallel to a measuring thermal resistance of a sample $R_s$ and a second leakage resistance $R_{lc}$ is added in parallel to a measuring thermal resistance of a reference $R_r$, thereby decreasing the effective resistance of the measuring thermal resistances.

34. The method of claim 33, wherein leakage resistance $R_{lc}$ of an empty differential scanning calorimeter cell represents a combination of radiation and gas conduction between the sensor of the differential scanning calorimeter and the enclosure.

35. The method of claim 31, wherein calibration is performed with first and second calibration samples without pans placed on respective sample and reference sides of the DSC, and a leakage thermal resistance $R_{lr}$ between the first calibration sample and an enclosure is added in parallel to a measuring thermal resistance of the sample calorimeter, and a leakage thermal resistance $R_{ls}$ between the second calibration sample and an enclosure is added in parallel to the measuring thermal resistance of the reference calorimeter.

36. The method of claim 31, wherein leakage thermal resistances associated with heat leakage are calculated prior to performing calibration.

37. The method of claim 36, wherein the leakage thermal resistances are computed using finite element analysis of the DSC, including an analysis of the interior of the enclosure, sample pans, and the sensor.

38. A DSC system comprising:
  (a) a DSC cell comprising a sample calorimeter and a reference calorimeter, and a base;
  (b) temperature sensors for measuring differential temperatures between a sample position in the sample calorimeter, a reference position in the reference calorimeter and the base, said sensors producing analog signals representative of said differential temperatures; and
  (c) analog-to-digital converters for converting the analog signals to digital signals, and providing the digital signals to a microprocessor,
  wherein said microprocessor comprises a thermal network model for calculating heat flow to the sample, and
  wherein said thermal network model accounts for effects of sensor asymmetry, sample and reference pans, and heat leakage, wherein heat leakage is accounted for in calibration of the sensors in the DSC.

39. The DSC system of claim 38, wherein the thermal network model includes thermal resistances and thermal capacitances representing the effects of contact resistances, heat leakages, and heat capacities.

40. The DSC system of claim 38, further comprising means for measuring the actual heat flow to the sample.

41. The DSC system of claim 38, wherein the actual heat flow to the sample is measured using the equation:

$$\dot{q}_{sam} = \dot{q}_s\left(1 + \frac{R_{ps}}{R_{ls}}\right) + \frac{\Delta T_0}{R_{ls}} - \left(\frac{m_{ps}\dfrac{dT_{ps}}{dt}}{m_{pr}\dfrac{dT_{pr}}{dt}}\right)\left(\dot{q}_r\left(1 + \frac{R_{pr}}{R_{lr}}\right) + \frac{\Delta T_0 + \Delta T}{R_{lr}}\right),$$

wherein $q_s$ is a measured sample heat flow, $q_r$ is a measured reference heat flow, $R_{ps}$ is a thermal resistance between a sample pan and a sensor, $R_{pr}$ is a thermal resistance between a reference pan and the sensor, $R_{ls}$ is a thermal resistance for heat leakage for a sample pan, $R_{lr}$ is a thermal resistance for heat leakage for a reference pan, $\Delta T_o$ is a temperature difference between a sample position and a position of the base of the sensor, $\Delta T$ is a temperature difference between the sample and reference positions, $dT_{ps}$ is a change in temperature in the sample pan, $dT_{pr}$ is a change in temperature in the reference pan, $m_{ps}$ is a mass of the sample pan, and $m_{pr}$ is a mass of the reference pan.

42. A DSC system comprising:
  means for calibrating measuring thermal resistances and heat capacities of the DSC, such means accounting for thermal resistances associated with heat leakage;
  means for operating the differential scanning calorimeter; and
  means for calculating the heat flow to the sample
  wherein the first differential temperature measures one of a temperature difference between a sample position and a base position, a temperature difference between a reference position and the base position, and a temperature difference between the reference position and the sample position, and wherein the second differential temperature detector measures a second one of the temperature difference between the sample position and the base position, the temperature difference between the reference position and the base position, and the temperature difference between the reference position and the sample position, and wherein the second differential temperature detector measures the third one of the temperature difference between the sample position and the base position, the temperature difference between the reference position and the base position, and the temperature difference between the reference position and the sample position.

* * * * *